United States Patent [19]

Meline et al.

[11] Patent Number: 4,879,906
[45] Date of Patent: Nov. 14, 1989

[54] VIBRATION DAMPED MOUNTING FOR EXTENSOMETER SYSTEM

[75] Inventors: Harry R. Meline, Minnetonka; Richard A. Meyer, Carver; Nebojsa D. Kovacevic, Plymouth, all of Minn.

[73] Assignee: MTS Systems Corporation, Eden Prairie, Minn.

[21] Appl. No.: 226,423

[22] Filed: Jul. 29, 1988

Related U.S. Application Data

[63] Continuation-in-part of Ser. No. 186,367, Apr. 26, 1988.

[51] Int. Cl.$^4$ .......................... G01B 5/30; G01N 3/08; G01N 17/00
[52] U.S. Cl. ....................................... 73/826; 33/787; 73/430; 374/55
[58] Field of Search .................... 374/55, 46, 47, 49; 73/826, 781, 855, 430; 33/147 D, 787, 788, 789, 790

[56] References Cited

U.S. PATENT DOCUMENTS

| | | | |
|---|---|---|---|
| 2,336,286 | 12/1943 | Owen | 374/55 |
| 2,545,482 | 3/1951 | Manjoine et al. | 33/788 |
| 3,001,291 | 9/1961 | Sjostrom | 338/6 X |
| 3,254,741 | 6/1966 | Greene, Jr. | 73/430 X |
| 3,385,097 | 5/1968 | Green | 374/55 |
| 3,960,009 | 6/1976 | Roepke et al. | 73/784 |
| 4,522,066 | 6/1985 | Kistler et al. | 73/855 X |
| 4,525,081 | 6/1985 | Myhre | 73/430 |
| 4,527,335 | 7/1985 | Meline | 33/787 |
| 4,535,636 | 8/1985 | Blackburn et al. | 374/55 X |
| 4,537,082 | 8/1985 | Meline et al. | 33/787 |
| 4,607,531 | 8/1986 | Meline et al. | 73/794 |

OTHER PUBLICATIONS

MTS–"Grips and Fixtures Catalog," ASTM E8, pp. 1–31 (in brochure), MTS System Corporation, 1986.

*Primary Examiner*—Daniel M. Yasich
*Attorney, Agent, or Firm*—Kinney & Lange

[57] ABSTRACT

An extensometer support system having vibration damping mountings for parts that have substantial mass and which are subjected to external vibrations. Such parts include counterweights for counterbalancing the extensometer and also the mounting for an external support frame for the extensometer. The vibration damping comprises a mounting made of a suitable damping material, such as a silicone foam rubber.

11 Claims, 8 Drawing Sheets

VIBRATION DAMPED MOUNTING FOR EXTENSOMETER SYSTEM

CROSS-REFERENCE TO RELATED APPLICATION

This application is a continuation-in-part of copending application Ser. No. 07/186,367, filed Apr. 26, 1988.

BACKGROUND OF THE INVENTION

1. Field of the Invention

The present invention relates to a damped support system for extensometers which have masses which are subjected to external vibrations.

2. Description of the Prior Art

Extensometers which are supported by external members (other than the specimen) are subjected to vibrations induced by external forces, such as accidentally hitting the external support. The support system has a mass, and where counterweights are provided, the external vibrations induced do not damp down quickly, and the extensometer output is adversely affected.

In high temperature extensometers, the sensing extensometer is coupled to the specimen by long ceramic rods which engage the specimen at contact points and which extend to sensor system supports that are independently supported from the test load frame. The specimen contact rods and the extensometers must be counterweighted to avoid placing external loads on the rods which can possibly result in slipping of the contract rods on the specimen. The support frame has substantially unrestrained movement in several degrees of freedom to accommodate shifts in the specimen during the process of heating up. Also, the ceramic specimen contact rods are counterweighted by suitable balance weights or masses that will tend to vibrate from external inputs.

SUMMARY OF THE INVENTION

The present invention relates to a vibration damped extensometer support and counterbalance system. The support system supports an extensometer assembly having specimen contact rods of substantial length. The support system is designed to accomodate movement of the specimen contact rods during initial warmup of the specimen in a furnace for high temperature tests. Parts of the support system require counterweights to insure that the support system does not induce loads at rest, which would affect strain readings or cause slippage.

As shown, a parallel linkage support frame for the specimen contact rods is used. The parallel linkage support frame is suspended on a support link from an external member such as a main load frame used for loading the specimen.

One of the specimen contact rods is supported relative to the parallelogram linkage support frame through a sensing system which senses differential movements of the outer ends of the specimen contact rods when the specimen is under strain. The weight of the one elongated specimen contact rod is counterweighted, as is conventional, and the mass of the counterweight will also vibrate after being initially excited by an external blow or impact and affect the output of the sensing system for a period of time.

The other of the specimen contact rods is supported on the parallel linkage support frame and the support frame carries a counterweight to counterbalance the second specimen contact rod. The frame counterweight will also tend to vibrate from impacts transmitted through the support frame mounting.

The flexure link supporting the parallelogram linkage support frame permits the entire support frame to move easily in direction parallel to the longitudinal axes of the elongated specimen contact rods. To isolate vibration of the support frame and to dampen induced vibrations, the support between the flexure link and the main external frame mount also includes a vibration isolating or damping material to reduce transmission of external vibrations to the flexure link and the sensing system and to damp external vibrations.

In a preferred embodiment, the mounting of each extensometer counterweight to its respective support is through a vibration damping material. Isolating the counterweight mass with damping material significantly reduces vibration problems. Using damping material for the frame support system further aids in reducing vibration problems.

As stated, one counterweight or mass is provided to counterbalance the moments created by gravity on the sensing specimen contact rod about an axis perpendicular to the longitudinal axis of the specimen. The rod is coupled through a sensing system to the support frame. The sensing system mounting for the one specimen contact rod is used to provide a signal indicating differential movement between the outer specimen engaging ends of the two specimen contact rods.

The counterweight on the parallelogram linkage support frame counterbalances the other specimen contact rod and is provided to avoid unwanted moments and to balance the support frame in its reference position.

The use of damping or vibration isolation materials for mounting counterbalancing weights is useful with all counterbalanced extensometers.

DETAILED DESCRIPTION OF THE PREFERRED EMBODIMENTS

Figure 1:
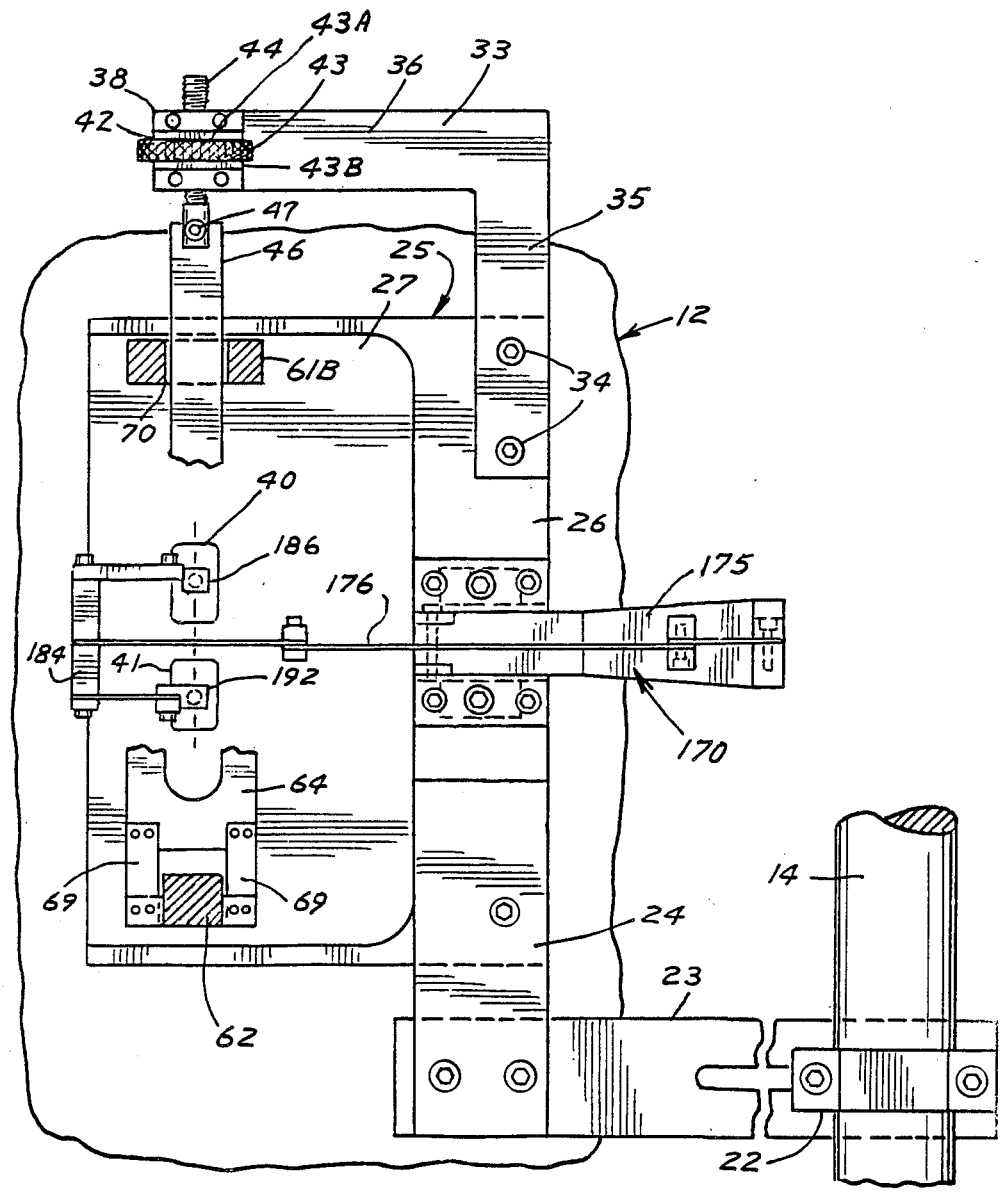
FIG. 1 is a fragmentary end view of a typical heat shield and main support for a high temperature extensometer made according to the present invention with parts shown fragmentarily looking toward an associated test furnace.
Figure 2:
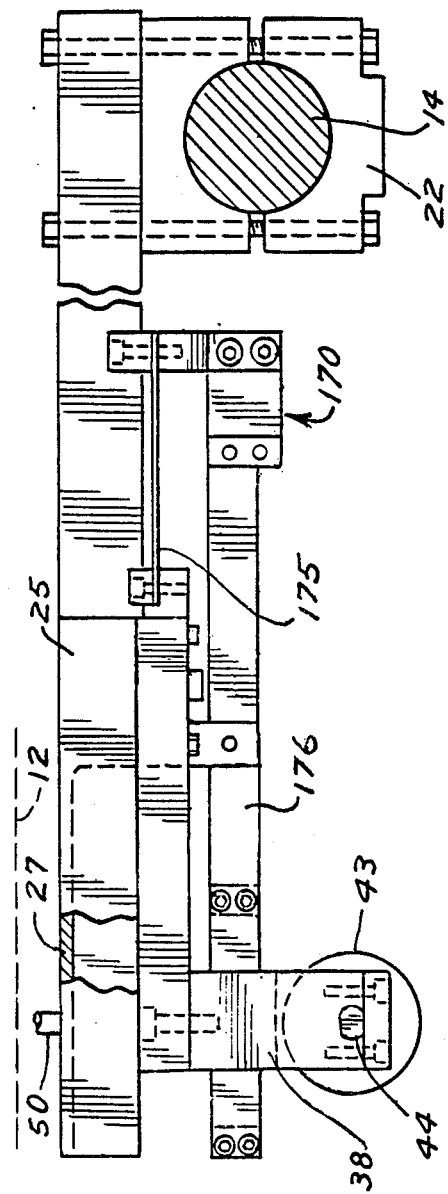
FIG. 2 is a top plan view of the device of FIG. 1 with a phantom representation of an associated test furnace illustrated, but not to scale.
Figure 3:
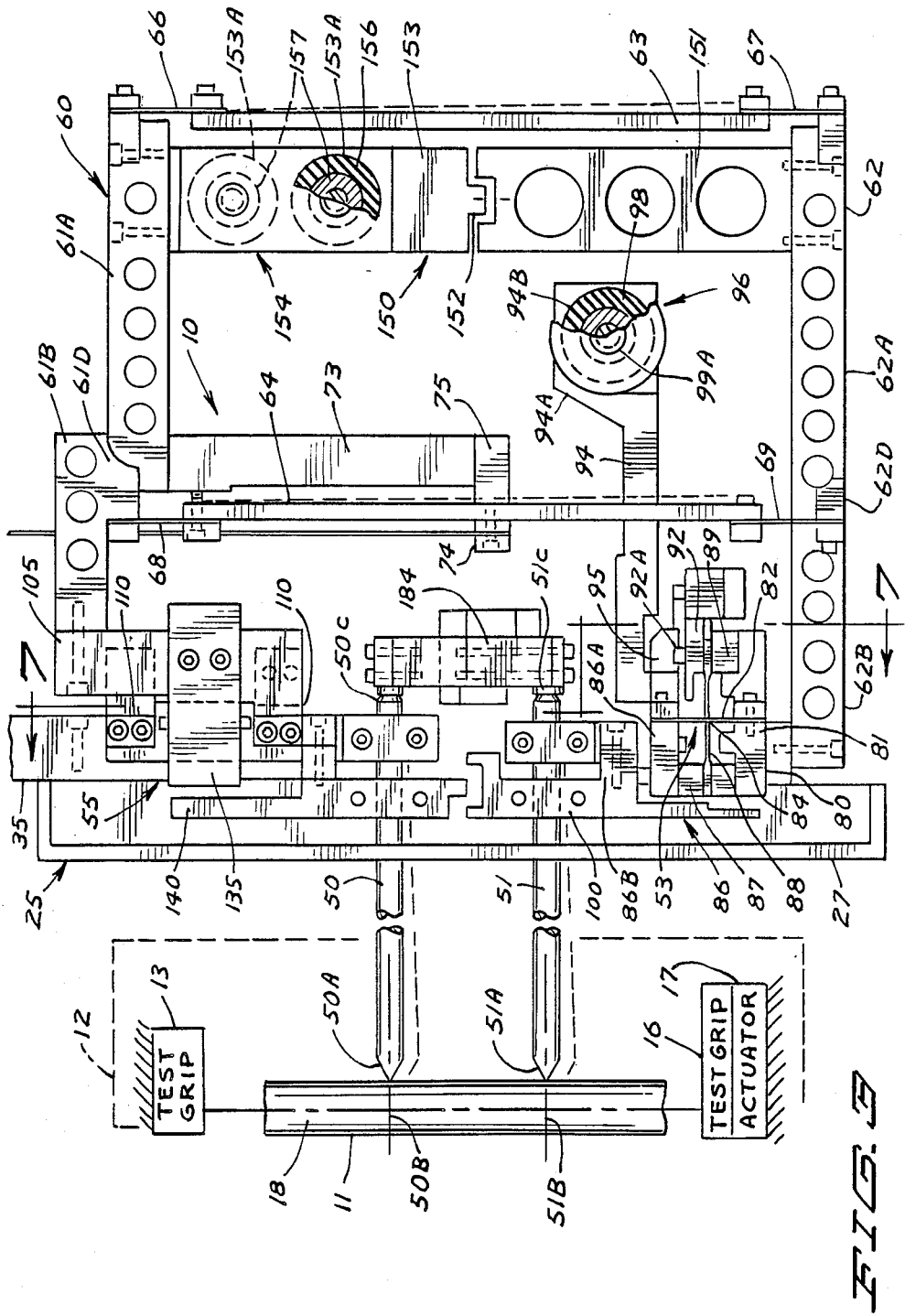
FIG. 3 is a side view of a parallelogram linkage support frame made according to the present invention supported from the main support shown in FIGS. 1 and 2 and showing elongated specimen contact rods engaging a specimen that is mounted in a furnace.

Referring to the drawings and the numerals of reference thereon, an extensometer assembly is indicated generally at 10 in FIG. 3, and it is of a type that is used to test a specimen indicated at 11 that is mounted adjacent to a heat source, such as being in a furnace represented in dotted lines at 12 in FIG. 3 and schematically represented in FIG. 1. The furnace 12 has suitable openings for operation with the extensometer and with a test load frame or testing machine. The furnace 12 is mounted with respect to a load frame comprising a pair of columns 14, one of which is shown only fragmentarily in FIGS. 1 and 2. A first specimen grip 13 (FIG. 3) is mounted on the load frame and a second load grip 16 is attached to an actuator 17 (FIG. 3) for loading the specimen 11 along its central axis 18 in the load frame. The extensometer assembly 10 is supported so that the strain sensing is accurate and so that the rods that contact the specimen are not likely to slip when the specimen 11 and the grips 13 and 16 move as the furnace is heated, or when the specimen 11 is loaded. In FIGS. 1 and 2, the main support is illustrated, fragmentarily. The column 14 forming part of the test load frame is used as a mounting member, and a split clamp indicated generally at 22 is clamped onto the column 14 and can be adjusted up and down. The split clamp in turn is used to support a support arm 23 that extends radially from the column. The arm 23 would be at an angle with respect to a line extending between a pair of columns 14 that are normally used in a load frame because the furnace 12 and specimen 11 are positioned between the load frame columns 14 and the main part of the extensometer assembly 10 is outside the furnace.

The arm 23 in turn supports an upright support block 24 that is attached to the arm 23 at its outer end as seen in FIGS. 1 and 2. The support block 24 is suitably attached to a unitary heat shield indicated at 25. The heat shield 25 is made of a suitable heat conducting material such as copper, and has internal passageways for cooling water. The heat shield 25 is made with a relatively thick side block 26, and a heat shield plate 27 that is attached to the block 26.

Additionally, an extensometer main support arm assembly indicated generally at 33 is mounted to the upper end of the block 26 with suitable cap screws 34. The extensometer support arm assembly 33 has an upright portion 35, and a laterally extending portion 36 that extends above the adjacent plate 27. A laterally extending arm 38 forming part of the arm assembly 33 is fixed to portion 36 and extends in a direction generally perpendicular to the plate 27. The arm 38 is positioned in alignment with a pair of apertures indicated at 40 and 41 in plate 27, which are used for permitting elongated specimen contact rods 50 and 51 (FIGS. 2, 3, 5 and 6) to pass through the heat shield into the furnace 12 to contact the specimen 11 being tested. The outer end of arm 38 has a horizontal slot 42 milled in it (FIG. 1). A knurled thumb wheel or nut 43 is placed in the slot 42, and a screw 44 is threaded in the knurled nut. The screw 44 has flat sides, and passes through openings in the arm 38 on opposite sides of the slot in which the knurled nut 43 is mounted. The screw 44 therefore will not rotate, but can be moved axially up or down by rotating the knurled nut.

For vibration isolation or damping, a pair of elastomeric material layers 43A and 43B are positioned on the top and bottom of the slot 42, to support and guide the knurled thumb wheel 43. The weight of the supported extensometer is supported on layer 43B. The damping material is selected to absorb vibration energy. The lower end of the screw 44 is bifurcated to receive a thin flexure support strap 46. The strap 46 is held on the end of the screw 44 with a cross pin 47 (FIG. 1). This also can be seen in FIG. 5, where the flexure strap 46 is shown along with the screw 44 and the knurled nut 43. The arm assembly 33 including the upright section 35 and the lateral section 36 is a unitary member that stably support overhead support arm 38.

Referring to FIG. 3, it can be seen that the extensometer assembly 10 includes a pair of elongated specimen contact rods 50 and 51. The first rod 50 is the upper rod as shown, and the second rod 51 is the lower rod. The outer ends 50A and 51A of the rods contact a specimen with an edge line or knife edge formed by suitably shaping the ends.

The lower specimen contact rod 51 is supported through a measuring sensor or sensing system indicated generally at 53 that is of substantially conventional design utilizing a cross flexure arrangement so that the rod 51, and in particular its outer end 51A, which is the specimen contact end, can pivot and move along the axis 18 of the specimen 11 relative to the outer end 50A of the rod 50 about a flexure pivot axis indicated generally at 54. The upper specimen contact rod 50 is supported on a contact rod support system 55, which comprises a cross-flexure arrangement for mounting the base end of the rod 50 for permitting movement of the outer end 50A of the specimen contact rod 50 about an axis generally parallel to the axis 18 of the specimen to be tested.

The support system 55 and the sensing system 53 which support the inner or base ends of the rods 50 and 51 are supported by a parallelogram linkage support frame indicated generally at 60, which includes a first link or beam 61 which as shown is an upper beam, and a second (lower) link or beam 62. The first and second beams 61 or 62 have beam sections 61A and 62A which are mounted parallel to each other, and which are held together with a third link or beam 63 and a fourth link or beam 64, which is parallel to the third beam 63. The third and fourth beams are joined to the first and second beams 61 and 62 to form the parallelogram linkage support frame 60. The beams 61 and 62 are joined to the third link 63 through a first flexure strap set 66 that comprises a pair of spaced apart coplanar spring straps that are flexible and which are joined at first ends to an end of first beam section 61A, and at second ends to the end of third beam 63. The opposite end of the third beam 63 is connected with a pair of flexible straps or flexures 67 to the outer end of the second beam section 62A. Straps 67 are fastened at their ends to the second beam section 62A and the third beam 63, respectively. The fourth beam 64 is connected with suitable flexure straps 68 to ears 61D integral with the first beam section 61A at an intermediate portion of the beam 61. The ears form the end of the first parallel link or beam section 61A. The lower end of the fourth link or beam 64 is connected with a pair of coplanar flexure straps 69 to a pair of ears 62D at an intermediate portion of the beam 62, which ears are at the end of second beam section 62A.

It can be seen therefore that the first and second (upper and lower) beams 61 and 62 can move axially independently of each other in direction parallel to the longitudinal axes 50B and 51B of the elongated specimen contact rods 50 and 51 as permitted by the hinging or pivoting action of the flexure straps 66, 67, 68 and 69. The straps form friction free, zero clearance (or looseness) hinges.

The upper beam section 61A forms the actual parallel beam or link that is connected to the third and fourth beams 63 and 64. A second arm or beam section 61B of beam 61 is integral with the parallel beam section 61A and extends toward the specimen and heat shield from the beam section 61A. The beam or arm section 61B has a substantially greater lateral width than the beam section 61A, as shown perhaps best in FIG. 6, and has a central opening therethrough indicated at 70.

It should be noted that the beams of the parallelogram linkage support frame 60 have cross holes formed therein for weight reduction. These holes are seen in FIG. 3, for example. A counterweight assembly is used to balance the frame. The counterweight is mounted in a manner to achieve vibration isolation according to the present invention, as will be explained.

The flexure support strap 46 passes through the opening 70, and the lower end of strap 46 is mounted to a parallel linkage support frame arm 73 with a suitable clamp block 74 held in place with cap screws. The arm 73 has a base portion 75 (FIG. 3) which passes through an opening in the fourth beam or link 64. The arm 73 is positioned between the beams or links 63 and 64 as can be seen and is near the center of gravity of the extensometer assembly 10, so the assembly can be balanced when suspended from the support strap 46.

The flexure straps 68 are mounted on the ears 61D that are integral with the beam section 61B and on the lower side of the beam section 61B. The ears 61D extend laterally from the width of the beam section 61A. Flexure strap 46 permits relatively free movement of the entire parallelogram support frame linkage and the supported specimen contact rods 50 and 51 in direction parallel to the axes 50B and 51B of the specimen contact rods. The support strap 46 also will twist easily about its longitudinal axis which is parallel to the plane of the parallelogram linkage support frame.

The second beam section 62A corresponds to and is parallel to and aligned with the first beam section 61A of the first beam 61, and a section 62B of beam 62 extends outwardly toward the heat shield 25 and specimen beyond the fourth beam 64. The end of second beam section 62B adjacent the heat shield 25 supports the sensing system 53, which in turn supports the elongated specimen contact rod 51.

The sensing system 53 (FIG. 3) has two relatively movable members joined by a separate, pivot forming cross-flexure of substantially conventional design. The sensing system 53 includes a base member 80 that is fixedly connected to the beam section 62B and is spaced slightly thereabove. The base member 80 has ears 81 extending laterally of the beam section 62B and each of these ears 81 supports a first end of a separate flexure strap 82. The upper ends of the straps 82 are connected to a lower specimen contact rod support arm 86. The specimen contact rod support arm 86 has an upright column portion 86B extending upwardly to support the specimen contact rod 51.

Additionally, the specimen contact rod support arm 86 has a lower center portion 87 that is substantially centered between the two flexure straps 82, and extends down below the attachment points of the cap screws 85. Center portion 87 supports one end of a flexure strap 88 that is a single strap that passes generally horizontally between the straps 82, so that the planes of the straps 82 and strap 88 intersect along the pivot axis indicated at 54, and the opposite end of the flexure strap 88 from the center portion 87 is supported on a center support 89 formed on the arm 80, positioned between the ears 81, and thus extending between the flexure straps 82,82, back over a portion of the beam section 62B. The end of the flexure strap 88 that is attached to the center support 89 is held in place with a suitable clamp block 92 and cap screws 92A.

The specimen contact rod 51 thus can pivot about axis 54 relative to the arm section 62B and the rest of the parallelogram linkage support frame. The flexure strap 88 has strain gages thereon to measure the bending of the strap and provide an output signal indicating movement of rod 51 relative to the arm 62B using known circuitry. Thus, the sensing system 53 is used to indicate relative movement of the rods 50 and 51 in direction of the loading axis of the specimen.

The support arm 86 also has a counterweight arm 94 mounted thereto on the top portion of a center block 95 fixed on the arm 86. The block 95 extends rearwardly above the clamp block 92 and is positioned so that it can move between the cap screws 92A that hold the block 92 in position to permit the required pivotal movement of arm 86 and rod 51 about pivot axis 54.

The counterweight arm 94 extends through an opening in the fourth beam 64 of the parallelogram linkage support frame and can move a limited amount up and down as the specimen contact rod 51 moves, which will in turn cause pivoting at axis 54 and thus movement of the block 95 and the counterweight arm 94.

Figure 4:
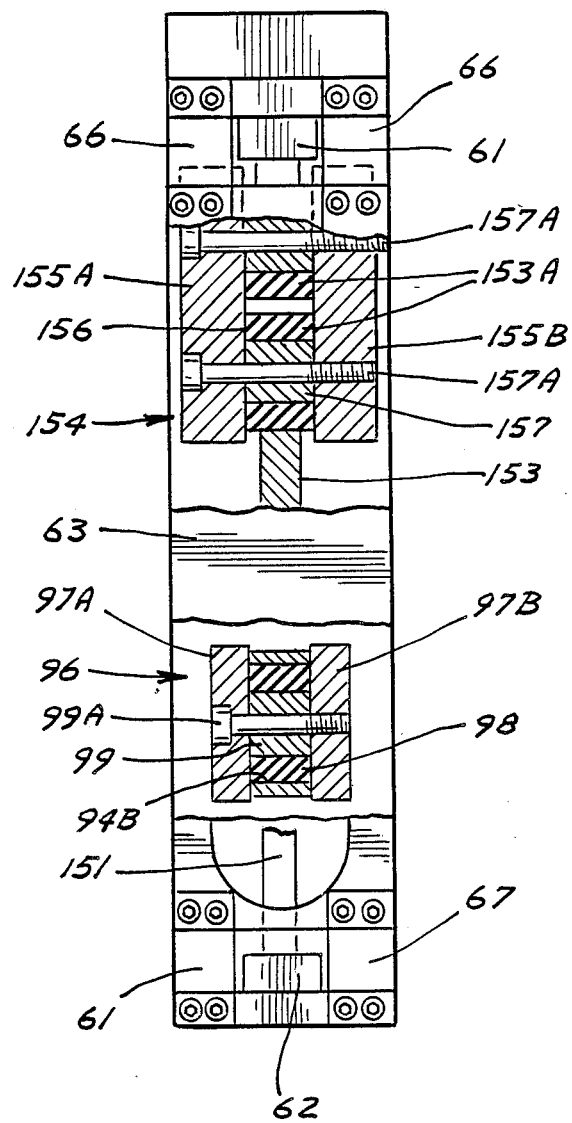
FIG. 4 is a rear view of the device of FIG. 3 with parts in section and parts broken away.

The outer end of counterweight arm 94 has an upright ear 94A fixed thereon which has a through bore 94B of substantial size. The bore is used for mounting a counterweight assembly indicated generally at 96 thereon. The counterweight assembly 96 is mounted with respect to the ear 94A, and thus with respect to the counterweight arm 94 and the rest of the sensing assembly, including the lower contact rod 51, through a damping material. As can be seen in FIG. 4, counterweight assembly 96 includes a pair of counterweights 97A and 97B (FIG. 4) that are mounted on opposite sides of the ear 94A. The counterweights 97A and 97B are supported with respect to the through bore 94B with a doughnut-shaped or annular band of damping material indicated at 98. This damping material 98 is preferably a material similar to a silicone foam rubber which has the ability to absorb vibrations and thus not transmit vibrations between the arm 94 and the mass of the counterweights 97A and 97B. The counterweights 97A and 97B are supported through a center bore of the ring of damping material 98 on a spacer tube 99, and then a cap screw 99A is passed through a bore in counterweight 97A and is threaded into a threaded opening in counterweight 97B so that the assembly is clamped in place. The damping material 98 supports both of the counterweights 97A and 97B. The spacer tube is slightly larger than the thickness of the ear 94A so the counterweights are spaced from the sides of the ear, and preferably the ring of damping material is compressed axially when the screw 99A is tightened down. This expands the damping material radially to tighten it in place.

In this way, the damping material is securely held in place and supports the counterweights. The counterweights are supported through the damping material that aborbs vibrations and reduces unwanted signals caused by shock loads occurring on the support system for the extensometer or some other external vibrations that might damage the signal. For example, if a hammer blow struck the test frame that is supporting the specimen, this impact will cause vibrations throughout the system, and instead of exciting the mass into a vibrating mode, the damping material will absorb these vibrations and dampen out the effects of such impact loads.

The ear 94A can be of any desired shape and size, as long as it has clearance, and the counterweight assembly 96 is such that it counterweights the weight of the lower specimen contact rod 51 which pivots about the pivot axis 54 formed by the cross flexure arrangement.

A secondary heat shield indicated generally at 100 is attached to the contact rod support arm 86, as shown, and thus the shield also is counterbalanced by counterweights 97.

The upper or reference specimen contact rod 50 is mounted on a flexure support that permits rod 50 to pivot about an axis parallel to axis 18 of the specimen 11, but rod 51 is rigidly mounted to the parallel linkage support frame 60 in relation to movement parallel to the axis 18. Thus specimen extension under load along axis 18 will cause movement of rod 51 relative to rod 50.

The specimen contact rod 50 is supported by the support flexure assembly 55 (see FIGS. 5 and 6) from the beam section 61B extending from the parallel beam section 61A with a depending support block 105. The flexure assembly 55 includes a pair of vertically spaced flexure straps 110, and these flexure straps are held clamped against a surface 111 with suitable clamp blocks held in place with cap screws. The flexure straps 110 extend forwardly (toward heat shield 25) as shown in FIG. 3 and are clamped onto an arm 115 with suitable clamp blocks 116.

Figure 6:
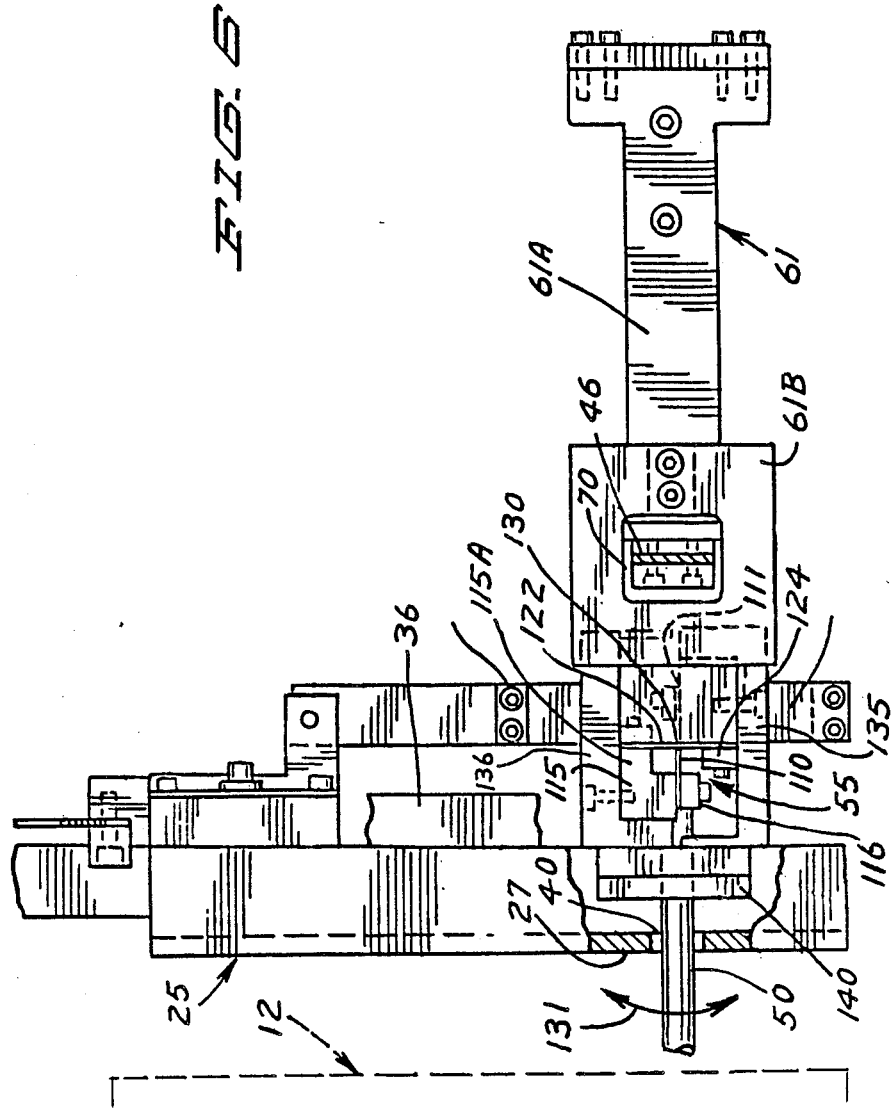
FIG. 6 is a top plan view of the device of FIG. 5.

The arm 115 has a lower end portion 117 that supports the specimen contact rod 50. The arm 115 is L-shaped as viewed from the top, as can be seen in FIG. 6, and has a leg portion 115A that provides a surface at right angles to the surface 111 on which a pair of flexure straps 122 are mounted. The flexure straps 122 have planes at right angles to the planes of flexure straps 110.

Figure 5:
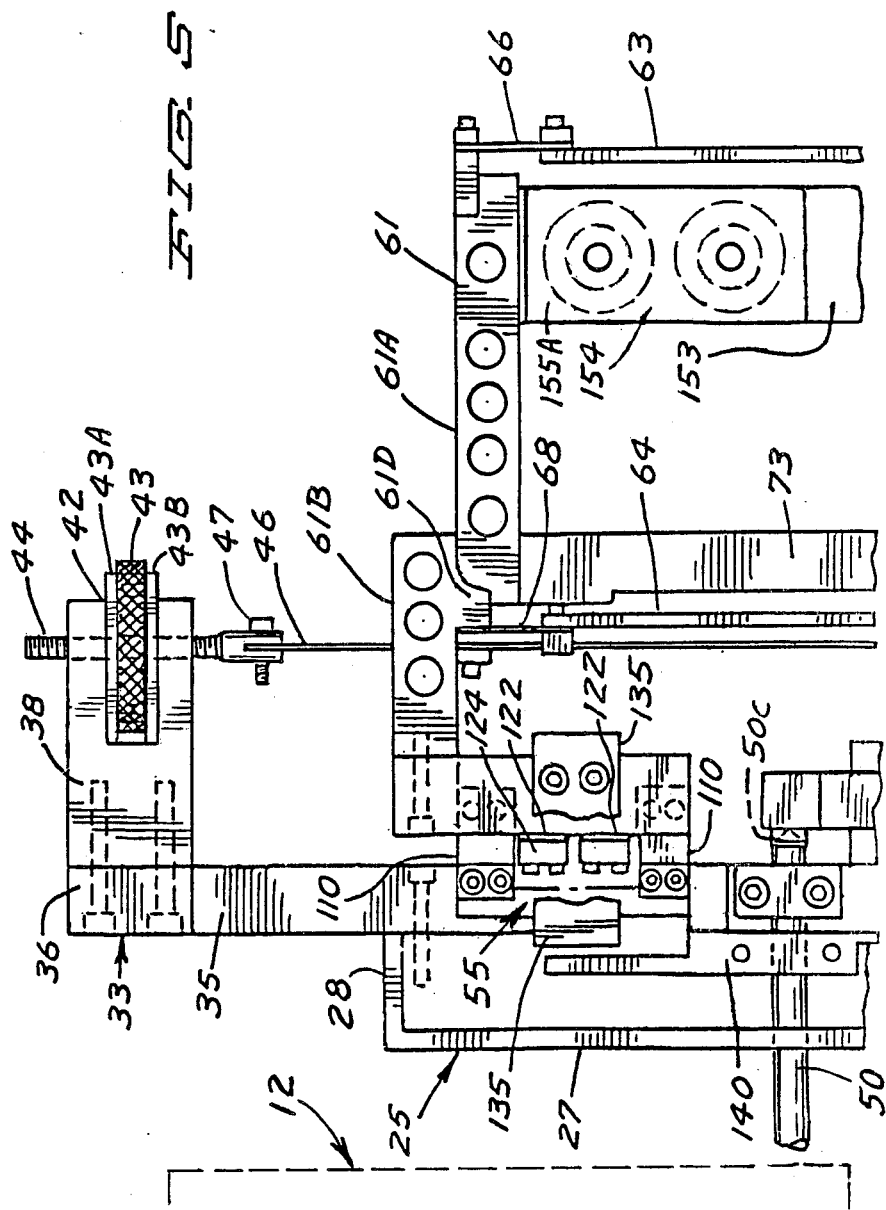
FIG. 5 is a fragmentary side view similar to that shown in FIG. 3 illustrating the top portion of the parallelogram linkage support frame, and the suspension system from the fixed support with a furnace location illustrated in dotted lines, but not to scale.
Figure 7:
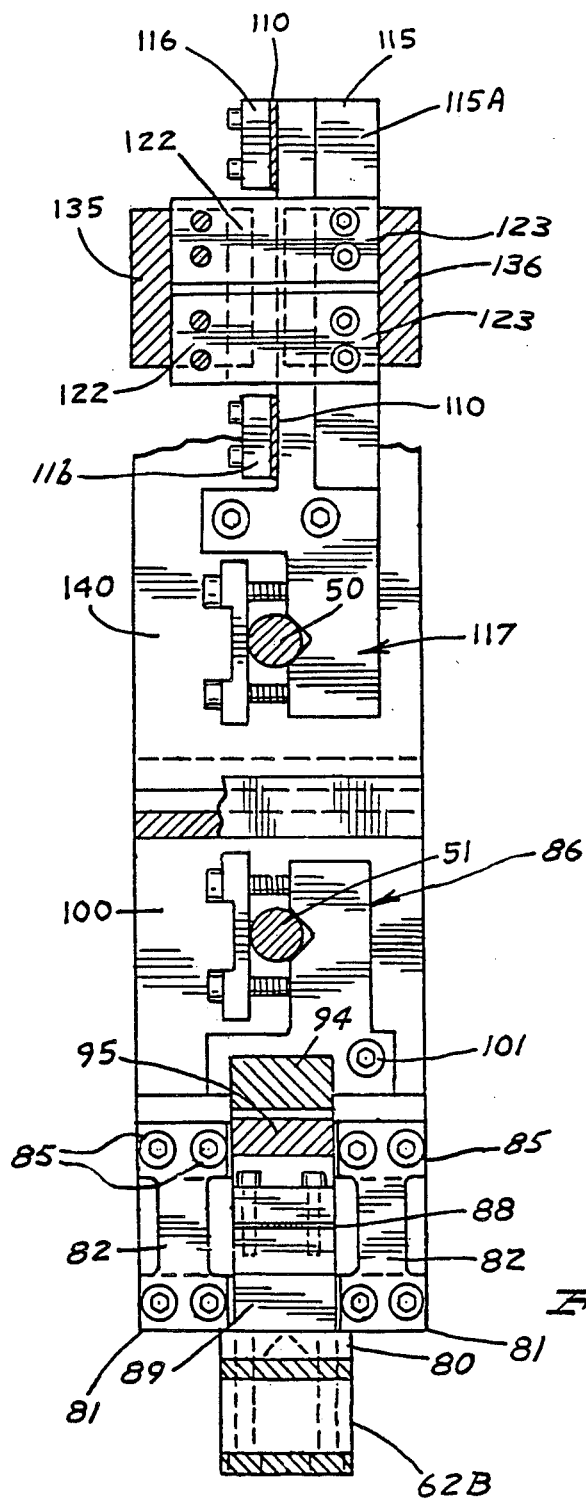
FIG. 7 is a sectional view taken as on line 7—7 in FIG. 3.

The flexure straps 122 are mounted with respect to a forward surface of a lower leg portion of block 105 with suitable clamp blocks 124 as can be seen in FIG. 5, as well as being supported with respect to the rearwardly facing surface of the leg 115A with suitable clamp blocks 123 (FIG. 7).

Thus, the two sets of flexure straps 110 and 122 intersect along a pivot axis shown in FIG. 6 at 130 and this permits the specimen contact rod 50 to move or pivot about axis 130 in directions as indicated by the arrow 131 in FIG. 6.

The amount of pivoting about axis 130 is to accommodate slight torsional movement of the specimen or the parallelogram linkage support frame 60. The weight of the specimen contact rods 50 and 51, the supports for the specimen contact rods, and the parallelogram linkage support frame 60 are all supported from the flexure strap 46.

The support block 105 and the arm 115 carry cooperating stops that will prevent excessive movement of specimen contact rod 50 about axis 130. The two stops are mirror images of each other and are indicated at 135 and 136, respectively. These stops can be made as desired.

An upper secondary heat shield 140 is clamped to the arm 115 and this adds weight to the same side of the strap 46 as the upper contact rod 50 and its support members.

A stop assembly 150 is provided at the rear portion of the parallelogram linkage support frame, and in particular extends between the first beam or section 61A, and the second beam section 62A. The stop assembly 150 includes an upright column 151 that is fixed to the second beam section 62A with suitable cap screws. A second stop column 153 is fixed to the first beam section 61A, and depends therefrom. The second stop column is in alignment with the stop column 151 as can be seen in FIG. 4. The upper end of column 151 and lower end of column 153 have an interfitting lug and receptacle forming a stop 152 to prevent excessive movement as the parallelogram linkage support frame moves too far out of a rectangular configuration, which is when right angles are formed between the axis of first and second parallel beam sections 61A and 62A and the third and fourth beams 63 and 64.

It also should be noted that the openings that are formed in the beams 61 and 62 are for weight reduction and to lower the mass of the frame. The members 151 and 153 also have openings therein.

The openings or bores indicated at 153A in FIG. 3 are used for mounting a counterweight assembly indicated generally at 154. This counterweight assembly is to counterbalance the weight of the frame on the opposite side of the strap 46 from the columns or stop members 151 and 153, and this includes the weight of the specimen contact rods, and the various supports for such contact rods. In order to reduce the undamped mass, and to provide for damping which will damp out externally induced vibrations and not start the counterweight assembly 154 to vibrate, the counterweight assembly is mounted to column 153 with suitable damping material. As shown, the counterweight assembly 154 includes a pair of counterweights 155A and 155B (see FIG. 4), with one on each of the opposite sides of the column 153. The openings or bores 153A have doughnut-shaped rings of damping material indicated generally at 156, which fit snugly within the bores, and which have spacer sleeves 157 on the interior. The spacer sleeves 157 have an axial length which is greater than the width of the column 153, and the doughnut or ring of damping material 156 likewise has a greater axial length than the width of the column 153. The counterweights 155A and 155B are then clamped against the spacer sleeves 157 using suitable cap screws 157A. The cap screws 157A pass through an opening in counterweight 155A and thread into an opening in counterweight 155B.

It can be seen that two openings 153A are provided in column 153 for mounting the counterweights, so there are two spacer sleeves, and two cap screws 157A. The counterweights can be clamped tightly against the end surfaces of the spacer sleeves 157 and the ring of damping material will be slightly compressed as the cap screws are tightened.

The ring of damping material can be made of a suitable silicone foam rubber, for example, and this will dampen vibrations that are induced from external effects, such as a blow to the testing frame, or even an accidental impact to the specimen, the mounting grips, or the loading actuator. Vibrations can be transmitted through the specimen contact rods and their mounting structures, and having the counterweight mass mounted through a damping material absorbs the energy of the vibrations and reduces the continued vibration of the larger mass of the counterweights.

It can thus be seen that the support strap 46 provides a vertical support for the entire parallelogram linkage support frame 60, the sensing system 53 and rod 51, and the support for the upper specimen contact rod 50. The support frame 60 is free to move in direction of the axes 50B and 51B of the specimen contact rods 50 and 51. The specimen contact rods 50 and 51 are urged toward the specimen 11, through a hold down flexure assembly indicated at 170 that provides a spring or biasing load from a flexure strap spring 175 against the base ends of the specimen contact rods 50 and 51, tending to move them toward the specimen. (Hold down flexure assembly 170 is also made to accommodate differential axial movement of the specimen contact rod 50 and 51 without substantial restraint (as can the parallelogram linkage support frame), and also twisting of the rods about an axis extending between the specimen contact rods. The flexure spring strap 175 of the hold down flexure assembly 170 is mounted to the upright block 26 of the heat shield 25. A flexure strap 176 extends over toward the specimen contact rods. The flexure strap 176 is oriented with its plane at 90° to the flexure spring strap 175.

The flexure spring strap 175 urges flexure strap 176 toward the specimen. The strap 176 carries a loading frame 184 at its outer end that has members 186 and 192 that engage the ends of the specimen contact rods. The spring force on members 186 and 192 urges the specimen contact rods toward the specimen. The flexure strap 176 permits up and down movement of the loading frame 184 and the flexure strap spring 175 exerts an axial load on the specimen contact rods.

The members 186 and 192 have conical surfaces that engage conical end surfaces 50C and 51C of the specimen contact rods 50 and 51.

The hold down flexure assembly 170 accommodates movements of the specimen contact rods 50 and 51 without causing erroneous readings or loads.

As the specimen is heated up (in a high temperature test), and the specimen supporting grips are also heated the specimen can shift substantially relative to the support of flexure strap 46. The shifting will be accommodated without adding bending strain to the ceramic rods because the parallelogram linkage support frame can parallelogram in its plane through the flexures 66, 67, 68 and 69 that hingedly connect the parallel beams together. Other motions of the specimen contact rods are also accommodated in the hold down flexure assembly 170, such as differential axial movement of the rods. Torsion of the specimen or twisting of the frame is accommodated by the upper contact rod support system 55 that supports the upper contact rod 50 relative to the first beam 61. An adequate and controlled spring force can be applied axially on the specimen contact rods, without incurring any other loads on specimen contact rods that are unwanted.

Additionally, as the specimen shifts, so that the specimen rods 50 and 51 are at an angle relative to their supports and the parallelogram linkage support frame 60 has moved out of its rectangular arrangement, thumb wheel or nut 43 can be threaded to adjust the axial position of the support screw 44 and the support strap 46 to bring the parallel linkage frame 60 back to a rectangular shape.

The support frame 60 couples the reference specimen contact rod 50 to the movable or sensing rod 51 through a measuring sensing system 53 to provide for strain measurement. The sensing system 53 can be any desired form that permits relative pivoting movement of the specimen contact rod 51 and provides an output signal indicating such movement. For example, capacitive sensing may be used between counterweight arm 94 and beam section 62A, because there is relative movement between these members, or an LVDT also could be used to sense movement caused by strain in the specimen.

Figure 8:
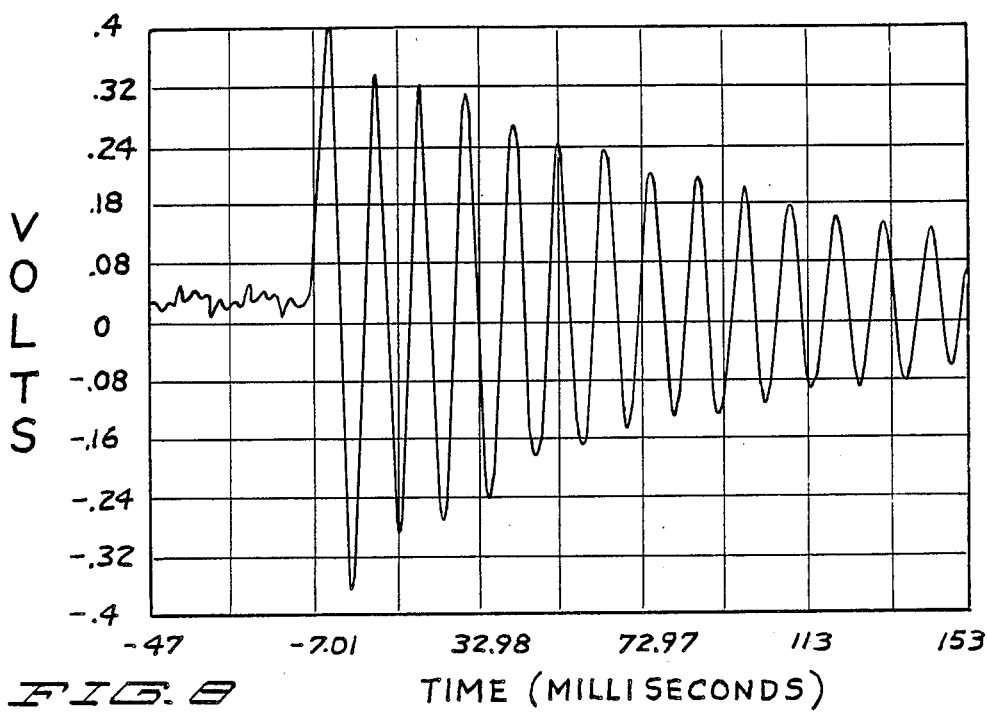
FIG. 8 is a typical plot of the output of a sensing system for an extensometer built as shown but without damping mountings when a test load frame is subjected to an impact.
Figure 9:
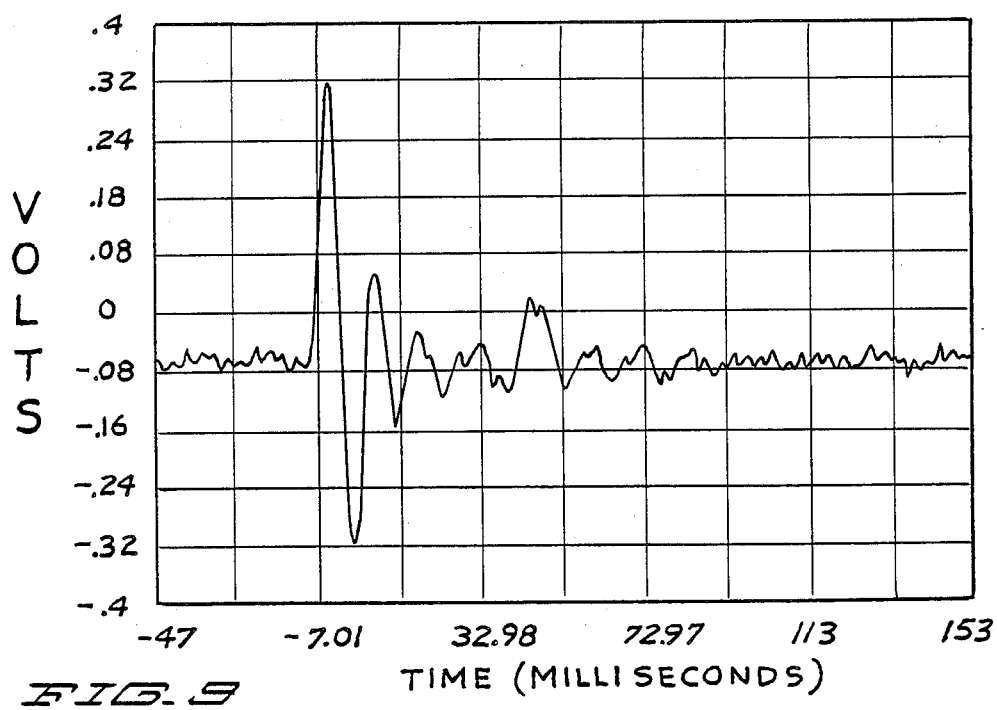
FIG. 9 is a plot of the output of the sensing for the same extensometer with the damping mounting disclosed used when the test load frame is subjected to substantially the same impact as in FIG. 8.

FIGS. 8 and 9 are graphic representations of outputs from the sensing assembly or sensing extensometer 53, showing the unwanted vibrations in FIG. 8 with undamped masses and counterweights for the lower assembly and for the frame. The counterweight assemblies will tend to vibrate, and as shown in FIG. 8, the signal output is affected for a significant time period. When both of the counterweights shown in the drawing are mounted using damping material (the damping material for the thumb wheel 43 was not used), FIG. 9 illustrates that the damping decreased the effect on the output significantly. The plots shown in FIGS. 8 and 9 are for the output signal from the sensing extensometer.

The addition of the damping material above for supporting the thumb wheel and thus for supporting the strap 46 adds additional damping isolation with respect to the main support for the extensometer.

The damping material also can be other selected materials.

Flexible urethane foam will work satisfactorily and other known foamed materials will work well.

The interface between the damping material and the support and counterweight is a friction joint that permits slight (micro) slipping to also absorb energy to provide the desired damping.

Although the present invention has been described with reference to preferred embodiments, workers skilled in the art will recognize that changes may be made in form and detail without departing from the spirit and scope of the invention.

What is claimed is:

1. An extensometer apparatus comprising means for contacting a specimen for use with the extensometer apparatus, a frame mounting the means for contacting the specimen, means for indicating movement of the specimen contact means with respect to a reference position, the extensometer apparatus including a mass supported on a movable member in the apparatus transmitting vibrations to the extensometer apparatus which affect an output of the means for indicating movement, and means for coupling the mass to the member comprising a layer of damping material mounting the mass relative the member so that vibrations are not directly transmitted to the mass except through the layer of vibration damping material.

2. The apparatus of claim 1 wherein the mass comprises a counterweight to counterbalance pivotal movements of a portion of the extensometer apparatus.

3. The apparatus as specified in claim 1 wherein the mass comprises a counterweight mounted to the frame for counterweighting portions of the frame with respect to a frame suspension member which is positioned between the specimen engaged by the specimen contact means.

4. The apparatus as specified in claim 1 wherein said mass comprises a support frame, means for supporting the support frame relative to a ground reference, and the means for supporting including the layer of damping material to couple the support frame to the ground reference.

5. The apparatus of claim 1 wherein the mass comprises a counterweight coupled to a pivoting, member on the support frame, the layer of damping material being mounted between the counterweight and the pivoting member.

6. An extensometer apparatus comprising a support frame for supporting at least two specimen contact means which have outer ends adapted to engage a specimen at spaced locations, and including means for indicating movement of the specimen contact means with respect to the loading axis of such specimen;

means for hingedly coupling the support frame relative to the specimen contact means so that the specimen contact means can pivotally move relative to the support frame as dimensional changes occur in such specimen;

a counterweight carried on the support frame and;

means for mounting said counterweight with respect to the support frame comprising a vibration damping material supporting the counterweight to carry weight induced loading between the support frame and the counterweight.

7. The apparatus as specified in claim 6 wherein said vibration dampening material comprises a silicone foam rubber.

8. The apparatus of claim 6 wherein the specimen contact means is mounted on a base and is elongated relative to the means for hingedly coupling, and means for mounting the counterweight on the base through the damping material to counterweight the elongated specimen contact means.

9. The apparatus of claim 6 and means for supporting the support frame relative to an external mount independently of coupling to a specimen, and a depending link that establishes a second pivot axis for the support frame, and wherein the counterweight is connected to the support frame to counterbalance the support frame relative to the second pivot axis.

10. An extensometer system comprising:

a support frame for supporting at least two specimen contact means which have outer ends adapted to engage a specimen in spaced location, and including means for indicating movement of the specimen contact means along the loading axis of such specimen, said support frame including a parallelogram linkage having first and second spaced apart substantially parallel beams, and third and fourth spaced apart substantially parallel beams positioned at right angles to the first and second beams;

means for hingedly coupling the third and fourth members to the first and second members at spaced locations thereon, respectively;

means for coupling a first of the specimen contact means to a first beam;

means for coupling a second of said specimen contact means to the second beam, including means for indicating movement of the outer end of said second specimen contact means in direction along a loading axis of such specimen to be tested, the specimen contact means having axes substantially parallel to the axes of said first and second beams at a reference position of the specimen contact rods; and vibration damping means for supporting at least certain portions of the mass of the extensometer system relative to other portions to damp vibrations induced in said such system.

11. The extensometer system of claim 10 and means for mounting the support frame with respect to an external mounting, said means for mounting including the vibration damping means for supporting the support frame.

* * * * *

UNITED STATES PATENT AND TRADEMARK OFFICE
CERTIFICATE OF CORRECTION

PATENT NO. : 4,879,906

DATED : November 14, 1989

INVENTOR(S) : Harry R. Meline et al

It is certified that error appears in the above-identified patent and that said Letters Patent is hereby corrected as shown below:

Column 11, line 8, after "pivoting" delete ",".

Signed and Sealed this

Sixth Day of November, 1990

*Attest:*

HARRY F. MANBECK, JR.

*Attesting Officer*      *Commissioner of Patents and Trademarks*